United States Patent [19]

Yen

[11] 4,013,667

[45] Mar. 22, 1977

[54] 2,2-DIARYL-3-(1-AZABICYCLO[2.2.2]OCT-2-YL)PROPIONAMIDES AND INTERMEDIATES THERETO

[75] Inventor: Chung H. Yen, Skokie, Ill.

[73] Assignee: G. D. Searle & Co., Chicago, Ill.

[22] Filed: Mar. 8, 1976

[21] Appl. No.: 664,723

[52] U.S. Cl. .......................... 260/293.53; 424/267
[51] Int. Cl.$^2$ ....................................... C07D 453/02
[58] Field of Search ............................ 260/293.53

[56] References Cited

UNITED STATES PATENTS

| | | | |
|---|---|---|---|
| 3,542,791 | 11/1970 | Moffett | 260/294.7 |
| 3,560,510 | 2/1971 | Warawa | 260/293 |
| 3,833,592 | 9/1974 | Papanastassiou et al. | 260/292 |

Primary Examiner—G. Thomas Todd
Attorney, Agent, or Firm—John J. Kolano

[57] ABSTRACT

This invention encompasses novel 2,2-diaryl-3-(1-azabicyclo[2.2.2]oct-2-yl)propionamides and intermediates thereto. These compounds are useful anti-diarrheal agents which possess little or no analgesic activity.

3 Claims, No Drawings

2,2-DIARYL-3-(1-AZABICYCLO[2.2.2]OCT-2-YL)PROPIONAMIDES AND INTERMEDIATES THERETO

The present invention is concerned with 2,2-diaryl-3-(1-azabicyclo[2.2.2]oct-2-yl)propionamides and intermediates thereto. More particularly, this invention is concerned with compounds of the formula

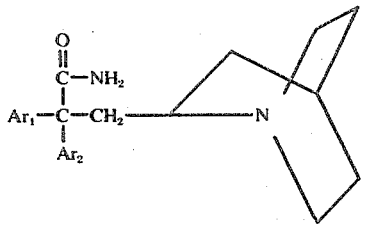

(dl)     (I)

wherein $Ar_1$ and $Ar_2$ are independently selected from the group consisting of phenyl, monosubstituted halophenyl and monosubstituted lower alkylphenyl, wherein the lower alkyl radicals contain 1 to 6 carbon atoms and may be alike or different.

A particularly preferred compound of this invention is that of formula (I) wherein both $Ar_1$ and $Ar_2$ are phenyl radicals.

The halo atoms encompassed by formula (I) include fluoro, chloro, bromo and iodo atoms. The lower alkyl radicals contain 1 to 6 carbon atoms and are exemplified by methyl, ethyl, propyl, butyl, pentyl, hexyl and the corresponding branched chain isomers thereof.

The point of attachment of the halo or alkyl substituent is not critical. Thus, the substituent may be in an ortho, meta or para position.

Equivalent to the compound of formula (I) for the purposes of the invention are the pharmaceutically acceptable acid addition salts thereof. Such acid addition salts can be derived from a variety of inorganic and organic acids such as sulfuric, phosphoric hydrochloric, hydrobromic, hydroiodic, sulfamic, citric, lactic, pyruvic, oxalic, maleic, succinic, tartaric, cinnamic, acetic, benzoic, salicylic, gluconic, ascorbic and related acids.

The compounds of the present invention are useful in consequence of their valuable pharmacological properties. They are, for example, potent anti-diarrheal agents as evidenced by their ability to inhibit gastrointestinal motility as set out in the following tests:

CHARCOAL MEAL TEST

The method used for this assay is a modification of the techniques previously described by Macht and Barba-Gose, J. Amer. Pharm. Ass., 20, 558 (1931), and Janssen and Jageneau, J. Pharm. Pharmacol., 9, 381 (1957). Details are as follows:

A group of six, male Charles River mice weighing 20-25 g. which have been previously fasted for 24 hours are pretreated with the test compounds administered orally as a solution in water or suspended in 0.5% methyl cellulose. A constant volume of 10 ml./kg. is employed. Thirty minutes following administration of the test compounds, the animals are given a single oral dose of charcoal which consists of 0.2 ml. per mouse of 10% charcoal suspended in 1.0% methyl cellulose. Three and a half hours after charcoal administration, the animals are sacrificed and the cecum examined for the absence or presence of charcoal on an all-or-none basis.

The median effective dose ($ED_{50}$) is then calculated for each compound using the logistic method of Berkson (1953).

Castor Oil-Induced Diarrhea in the Rat

Adult Charles River male rats are fasted in community cages for 24 hours prior to the test, with free access to water. The test compound is then administered intragastrically (suspended on 0.5% methyl cellulose) one hour prior to the intragastric administration of a dose of 1.0 ml. castor oil per rat. The rats are then observed for the presence or absence of diarrhea at hourly intervals for up to 8 hours past the castor oil administration. Using the method of Berkson (1953), the median effective dose ($ED_{50}$) values are calculated at each hourly interval for the test compound. The compounds of this invention advantageously demonstrate little or no analgesic activity at the test doses. The assessment of this activity is conducted by the following assay:

Tail Clip Test

A special clip is applied to the base of the tail of an adult male mouse weighing 18-25 grams and the time for the animal to turn around to bite at the clip is measured. The sensitivity of each mouse is determined one-half hour prior to drug administration and only those mice attempting to bite the clip are included in the experiment. The test compound is then administered either intragastrically or intraperitoneally and the response to placement of the clip is determined at 30, 60, 90 and 120 minutes after treatment. A response is considered positive if the animal takes more than 2 times the pre-drug time to bite at the clip at any of these time intervals. A test compound is considered active when 50 percent or more of the animals used show a positive response.

A representative compound of this invention which is particularly active in the Charcoal Meal Test anti-diarrheal assay is 2,2-diphenyl-3-(1-azabicyclo[2.2.2]oct-2-yl)propionamide. At a dose of 100 mg./kg. this compound shows no analgesic effects.

The compounds of formula (I) may be combined with various pharmaceutical carriers to provide compositions suitable for use in the treatment of diarrhea. The dosage of these compounds is dependent upon various factors, such as the compound employed and the particular response obtained. Typical dosages for use as an anti-diarrheal agent vary from 0.1 to 25 mg./kg. per day administered orally.

The compounds of the present invention are conveniently prepared according to the procedure illustrated by Scheme A.

Scheme A

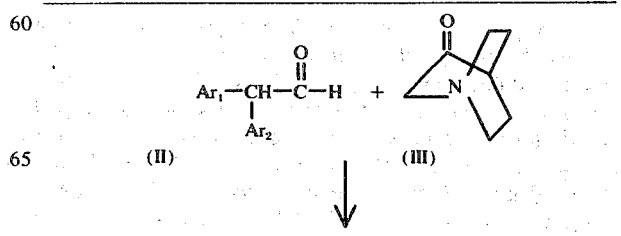

(II)     (III)

Scheme A-continued

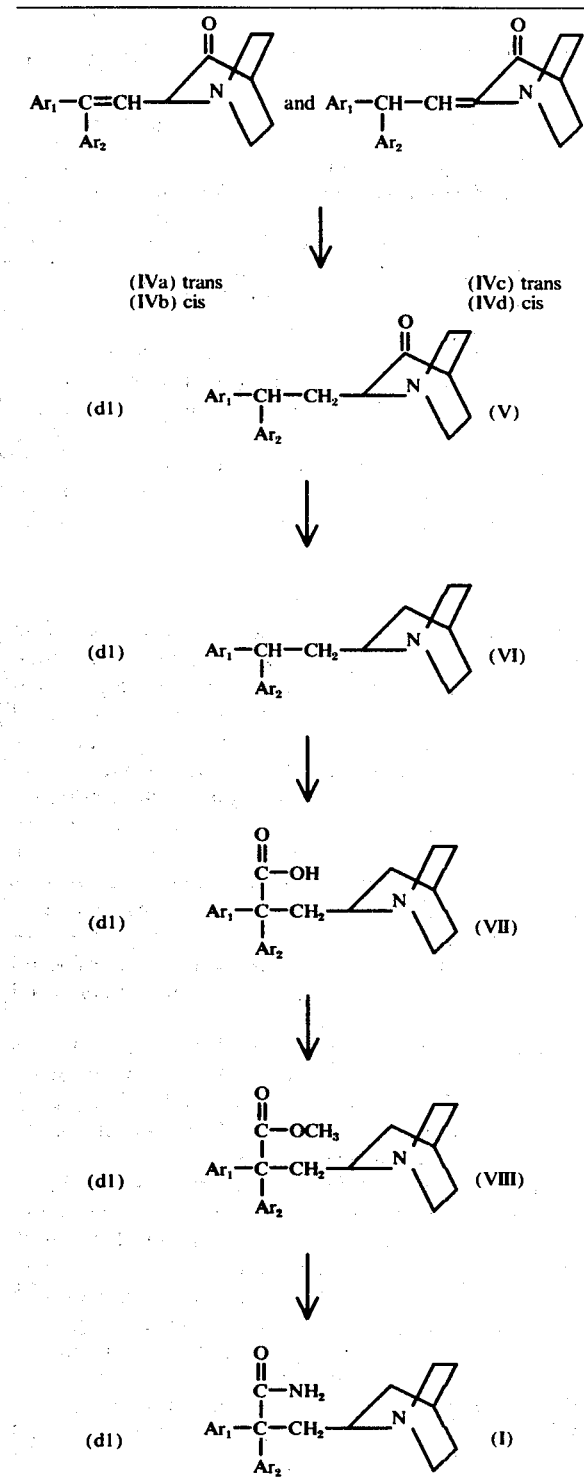

By way of illustration, the first step of Scheme A is shown by the condensation of diphenylacetaldehyde with 1-azabicyclo[2.2.2]octan-3-one. This reaction is conveniently conducted in an organic solvent, a particularly preferred solvent being methanol. This reaction produces a mixture of isomers illustrated by formulas IVa – IVd which, when subjected to catalytic hydrogenation, produce the 2-(2,2-diarylethyl)-1azabicyclo[2.2.2]octan-3-ones of formula (V).

The oxo group of the compounds of formula (V) is then reduced using a hydrazine hydrate and a base according to the Wolff - Kishner method. The resulting compounds of formula (VI) are then treated with butyl lithium in the presence of N,N,N',N'-tetramethylethylenediamine and carboxylated by bubbling carbon dioxide through the reaction mixture to afford the compounds of formula (VII).

The carboxy functional group of the compounds of formula (VII) is then esterified using a solution of methyl sulfate in methanol. The resulting compound of formula (VIII) is further converted to the desired 2,2-diaryl-3-(1-azabicyclo[2.2.2]oct-2-yl)propionamide of formula (I) by treatment with ammonia in the presence of a base. A particularly preferred base for use in this reaction is butyl lithium.

The novel intermediate of formula (VI) additionally exhibits anti-diarrheal activity in the Charcoal Meal Test, and, at a dose of 100 mg./kg. exhibits only slight analgesic effects.

The following examples describe in detail the preparation of compounds of the present invention. It will be apparent to those skilled in the art that many modifications, both of materials and method, may be practiced without departing from the purpose and intent of this disclosure. Throughout the examples hereinafter set forth, temperatures are given in degrees Centigrade (°C.) and relative amounts in parts by weight, except as otherwise noted.

EXAMPLE 1

64.8 Parts of 1-azabicyclo[2.2.2]octan-3-one hydrochloride and 100 parts diphenylacetaldehyde are suspended in 470 parts methanol and heated to boiling to form a solution. Then, 40.0 parts potassium hydroxide in 157 parts hot methanol is added with stirring. The hot solution is filtered and the solid collected is rinsed with 79 parts of methanol. The filtrate and the washing are combined and diluted with 860 parts of toluene. The resulting mixture is distilled until 1660 ml. of distillate is collected and a head temperature of 110° C. is reached. The pot residue is then diluted with 420 parts xylene, heated to reflux under a Dean-Stark collector for 40 minutes, cooled to room temperature, and the brown gum removed by filtration. After standing, the filtrate is decanted from the gummy precipitate which forms during standing, washed with water and dried over anhydrous sodium sulfate. Removal of the solvents under reduced pressure affords an oily residue which is dissolved in 130 parts ethyl ether and scratched to induce crystallization. The crystals are filtered, washed with ethyl ether and air-dried to give a first crop melting at about 141°-149° C. A second crop of crystals melting at about 100°-111° C. is isolated by reducing the volume of the mother liquors to 100 ml., diluting with 9 parts n-pentane, and cooling. Both crops of crystals are mixtures containing various amounts of the two isomers (cis and trans) of 2-(2,2-diphenylethylidenyl)-1-azabicyclo[2.2.2]octan-3-one, and 2-(2,2-diphenylethenyl)-1-azabicyclo[2.2.2]octan-3-one.

EXAMPLE 2

18.9 Parts of a mixture of the two isomers (cis and trans) of 2-(2,2-diphenylethylidenyl)-1-azabicyclo[2.2.2]-octan -3-one, and 2-(2,2-diphenylethenyl)-1-azabicyclo[2.2.2]-octan-3-one is dissolved in approximately 790 parts ethanol. Then, 4 parts of a 5% palladium-on-carbon catalyst is added and the mixture shaken in a Parr Shaker at room temperature and a pressure of 36–60 psi for 3 hours. The catalyst is removed by filtration and the solvents removed in vacuo. The residual white solid is dissolved in 560 parts of hot n-pentane. The solution is filtered and then concentrated on a steam bath to a volume of about 190 ml. Standing at room temperature affords a precipitate which is filtered, washed with n-pentane and dried in vacuo to provide a white solid. This solid is recrystallized from ethyl ether to afford 2-(2,2-diphenylethyl)-1-azabicyclo[2.2.2]octan-3-one. This compound begins to shrink at 103° C., clouds at 104°–105° C. and melts at about 107° C. and is represented by the following structural formula.

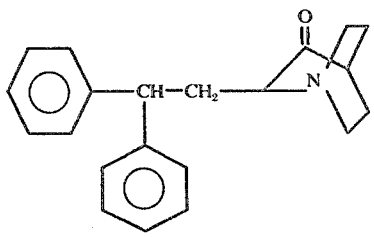

EXAMPLE 3

9.3 Parts 3-(2,2-diphenylethyl-1-azabicyclo[2.2.2]-octan-3-one, 1.30 parts potassium hydroxide, 3.6 parts by volume of a 85% solution of hydrazine in water, and 59 parts diethylene glycol are combined and refluxed, with stirring, under nitrogen for 2.75 hours. Stirring and heating are then discontinued and the reaction mixture is allowed to stand for 16 hours at which time the mixture is heated to distill until a head temperature of 235° C. is reached. After cooling to room temperature, the mixture is partitioned between 900 parts by volume of a 5% sodium chloride solution and two 430 parts portions of ether. The ethereal extracts are combined, washed with water, dried over anhydrous sodium sulfate and stripped in vacuo to give an oil which solidifies upon standing. This solid is crystallized from n-pentane to afford, as a white solid, 2-(2,2-diphenylethyl)-1-azabicyclo[2.2.2]-octane, melting at about 87.5°–89.0° C. This compound is represented by the following structural formula.

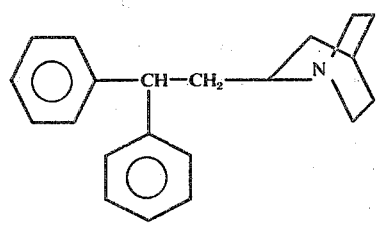

The white solid is dissolved in 71 parts of dry ether and treated with excess hydrogen chloride in isopropanol. The gum which precipitates solidifies and is filtered off and washed with ether. Recrystallization from a mixture of ethanol and ether affords 2-(2,2-diphenylethyl)-1-azabicyclo[2.2.2]octane hydrocloride, melting at about 218°–221° C.

EXAMPLE 4

To a mixture of 27.0 parts 2-(2,2-diphenylethyl)-1-azabicyclo[2.2.2]octane and 14.0 parts by volume N,N,N',N'-tetramethylethylenediamine in 220 parts dry cyclohexane is added 51 parts by volume of a 2.34 M solution of butyl lithium in hexane under nitrogen. The mixture is heated to reflux with stirring, for 2 hours resulting in a red mixture containing copious solid. After cooling to 10° C., carbon dioxide gas is bubbled through the mixture at about 10°–18° C. until a yellow-green solution is obtained. The solvents are then removed in vacuo and the residual solid is suspended in 1600 parts water. The suspension is washed with n-pentane, adjusted to pH 7 with aqueous sodium hydroxide, saturated with sodium chloride and repeatedly extracted with portions of dichloromethane. The dichloromethane extracts are combined, dried over anhydrous sodium sulfate and stripped in vacuo to afford an off-white solid. Recrystallization from benzene gives 2,2-diphenyl-3-(1-azabicyclo[2.2.2]oct-2-yl)propionic acid melting at about 180°–185° C. Further recrystallization from methyl ethyl ketone affords the above compound melting at about 184°–187° C.

The pure compound is treated with hydrogen chloride in isopropanol to give 2,2-diphenyl-3-(1-azabicyclo[2.2.2]-oct-2-yl)propionic acid hydrochloride melting at about 235°–237° C. with gas evolution after recrystallization from a mixture of ethanol and ethyl ether. This compound is represented by the following structural formula.

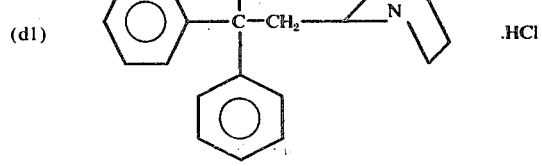

EXAMPLE 5

6.5 Parts of 2,2-diphenyl-3-(1-azabicyclo[2.2.2]-oct-2-yl)propionic acid hydrochloride is dissolved in 47 parts methanol. Then a solution of 0.7 part sodium hydroxide in 12 parts methanol is added, followed by 0.9 part 2,2-diphenyl-3-(1-azabicyclo[2.2.2]oct-2-yl)propionic acid and a solution of 2.7 parts methyl sulfate in 12 parts methanol. The resulting mixture is then refluxed for 20 minutes, cooled and stripped in vacuo. The gummy residue is partitioned between 90 parts by volume of a 2% sodium hydroxide solution and ethyl ether. The ether layer is separated, dried over anhydrous sodium sulfate and stripped in vacuo to afford as a gummy residue, methyl 2,2-diphenyl-3-(1-azabicyclo[2.2.2]oct-2-yl)propionate. The aqueous layer is adjusted to pH 7.9 with dilute hydrochloric acid, saturated with sodium chloride and extracted 6 times with portions of chloroform. The chloroform extracts are combined, dried over anhydrous sodium sulfate and stripped in vacuo to give 2,2-diphenyl-3-(1-azabicyclo[2.2.2]oct-2-yl)propionic acid (starting material). This solid is refluxed with 2.0 parts methyl sulfate and 35 parts methanol for 18 minutes and then worked up as before to afford a second yield of the desired methyl 2,2-diphenyl-3-(1-azabicyclo[2.2.2]oct-2-yl)propionate.

EXAMPLE 6

To a solution of 25 parts by volume liquid ammonia in 22 parts dry tetrahydrofuran is added dropwise over a 5 minute period 10 parts by volume of a 2.3 M solution of butyl lithium in hexane under reflux under a dry ice condenser. Then, a solution of 3.9 parts methyl 2,2-diphenyl-3-(1-azabicyclo[2.2.2]oct-2-yl)propionate in 18 parts dry tetrahydrofuran is added dropwise, with stirring. After stirring the resulting mixture under reflux for 3 hours the dry ice condenser is removed, and the mixture stirred at ambient temperature for a further two hours. The solvents are then removed in vacuo. The residual gum is suspended in water and extracted with a 1:1 ether-benzene solution. The ether-benzene extract is separated, washed with water, dried over anhydrous sodium sulfate and stripped in vacuo. The residue is triturated with 50 parts of n-pentane. The undissolved solid is filtered off, washed with n-pentane and air dried to give a white powder. This powder is recrystallized from a mixture of benzene and petroleum ether to afford, as white needles, 2,2-diphenyl-3-(1-azabicyclo[2.2.2]oct-2-yl)propionamide. This compound melts at about 192°–194° C. and is represented by the following structural formula.

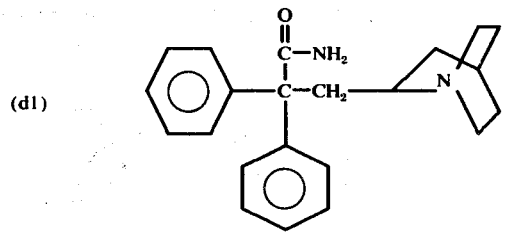

(d1)

EXAMPLE 7

Repetition of the procedures of Examples 1 and 2 using an equivalent quantity of bis(4-methylphenyl)acetaldehyde (prepared according to the procedure detailed in U.S.S.R. 173,783, CA 64:2005a) in place of the diphenylacetaldehyde affords 2[2,2-di(4-methylphenyl)ethyl]-1-azabicyclo[2.2.2]octan-3-one.

EXAMPLE 8

Substitution of an equivalent quantity of 2-[2,2-di(4-methylphenyl)ethyl]-1-azabicyclo[2.2.2]octan-3-one in the procedure of Example 3 affords 2-[2,2-di(4-methylphenyl)ethyl]-1-azabicyclo[2.2.2]octane.

EXAMPLE 9

When an equivalent quantity of 2-[2,2-di(4-methylphenyl)ethyl]-1-azabicyclo[2.2.2octane is used in the procedure of Example 4, there is obtained 2.2-di(4-methylphenyl)-3-(1-azabicyclo[2.2.2]oct-2-yl)propionic acid hydrochloride.

EXAMPLE 10

Use of an equivalent quantity of 2,2-di(4-methylphenyl)-3-(1-azabicyclo[2.2.2]oct-2-yl)propionic acid hydrochloride in the procedure detailed in Example 5 affords methyl 2,2-di(4-methylphenyl)-3-(1-azabicyclo[2.2.2]oct-2-yl)propionate.

EXAMPLE 11

Substantial repetition of the procedure detailed in Example 6 using an equivalent quantity of methyl 2,2-di(4-methylphenyl)-3-(1-azabicyclo[2.2.2]oct-2-yl)propionate affords 2,2-di(4-methylphenyl)-3-(1-azabicyclo[2.2.2]oct-2-yl)propionamide. This compound is represented by the following structural formula.

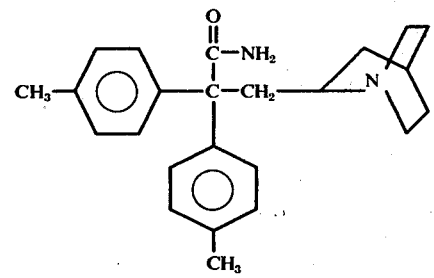

EXAMPLE 12

Repetition of the procedure detailed in Examples 1 and 2 using an equivalent quantity of bis(4-chlorophenyl)-acetaldehyde (prepared according to the procedure detailed in J. Med. Chem., 11 (2) 380–382 (1968) in place of the diphenylacetaldehyde affords 2-[2,2-di(4-chlorophenyl)ethyl]-1-azabicyclo[2.2.2]octan-3-one.

EXAMPLE 13

Substitution of an equivalent quantity of 2-[2,2-di(4-chlorophenyl)ethyl]-1-azabicyclo[2.2.2]octan-3-one in the procedure of Example 3 affords 2-[2,2-di(4-chlorophenyl)ethyl]-1-azabicyclo[2.2.2]octane.

EXAMPLE 14

When an equivalent quantity of 2-[2,2-di(4-chlorophenyl)ethyl]-1-azabicyclo[2.2.2]octane is used in the procedure of Example 4, there is obtained 2,2-di(4-chlorophenyl)-3-(1-azabicyclo[2.2.2]oct-2-yl)propionic acid hydrochloride.

EXAMPLE 15

Use of an equivalent quantity of 2,2-di(4-chlorophenyl)-3-(1-azabicyclo[2.2.2]oct-2-yl)propionic acid hydrochloride in the procedure detailed in Example 5 affords methyl 2,2-di(4-chlorophenyl)-3-(1-azabicyclo[2.2.2]oct-2-yl)propionate.

EXAMPLE 16

Substantial repetition of the procedure detailed in Example 6 using an equivalent quantity of methyl 2,2-di(4-chlorophenyl)-3-(1-azabicyclo[2.2.2]oct-2-yl)propionate affords 2,2-di(4-chlorophenyl)-3-(1-azabicyclo[2.2.2]oct-2 -yl)propionamide. This compound is represented by the following structural formula.

What we claim is:

1. A compound of the general formula

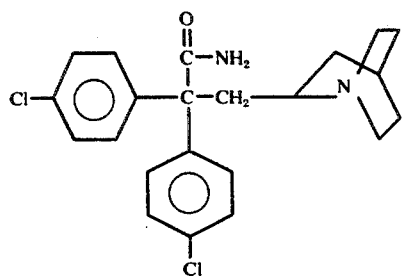

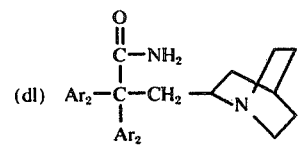

wherein $Ar_1$ and $Ar_2$ are independently selected from the group consisting of phenyl, monosubstituted halophenyl and monosubstituted lower alkylphenyl wherein the lower alkyl radicals contain 1 to 6 carbon atoms, and may be alike or different.

2. The compound according to claim 1 which is 2,2-diphenyl-3-(1-azabicyclo[2.2.2]oct-2-yl)propionamide.

3. The compound which is 2-(2,2-diphenylethyl)-1-azabicyclo[2.2.2]octane hydrochloride.

* * * * *